United States Patent [19]
Hasson

[11] Patent Number: 5,507,796
[45] Date of Patent: Apr. 16, 1996

[54] METHOD OF SUSPENDING A PELVIC ORGAN AND INSTRUMENT FOR PERFORMING THE METHOD

[76] Inventor: Harrith M. Hasson, 2043 N. Sedwick, Chicago, Ill. 60614

[21] Appl. No.: 235,553

[22] Filed: Apr. 28, 1994

[51] Int. Cl.⁶ .................................................. A61B 17/00
[52] U.S. Cl. ........................ 606/148; 606/139; 606/144; 606/208
[58] Field of Search ...................... 606/139, 142, 606/144, 145, 147–150, 1, 191, 198, 205–208; 128/20

[56] References Cited

U.S. PATENT DOCUMENTS

| | | | |
|---|---|---|---|
| 2,818,866 | 1/1958 | Thomas | 606/148 |
| 4,655,218 | 4/1987 | Kulik et al. | 606/205 |
| 4,819,640 | 4/1989 | Narayanan et al. | 606/148 |
| 4,911,164 | 3/1990 | Roth | 606/148 |
| 5,053,041 | 10/1991 | Ansari et al. | 606/148 |
| 5,129,912 | 7/1992 | Noda et al. | 606/148 |
| 5,192,280 | 3/1993 | Parins | 606/48 |
| 5,224,948 | 7/1993 | Abe et al. | 606/148 |
| 5,257,637 | 11/1993 | Gazayerli | 606/148 X |
| 5,282,826 | 2/1994 | Quaori | 606/207 |
| 5,342,374 | 8/1994 | Wan et al. | 606/148 |
| 5,342,375 | 8/1994 | Lemole | 606/148 |
| 5,360,428 | 11/1994 | Hutchinson, Jr. | 606/48 X |

FOREIGN PATENT DOCUMENTS

| | | | |
|---|---|---|---|
| 466632 | 1/1992 | European Pat. Off. | 606/148 |

*Primary Examiner*—Stephen C. Pellegrino
*Assistant Examiner*—Michael Peffley
*Attorney, Agent, or Firm*—Wood, Phillips, VanSanten, Clark & Mortimer

[57] ABSTRACT

A surgical instrument having a body, a tissue engaging and manipulating finger, and first structure for mounting the finger to the body. The finger has second structure thereon at first and second spaced locations to allow tissue engaged thereby to bridge the first and second spaced locations to allow a needle to be conveniently directed into a tissue engaged by the finger.

20 Claims, 2 Drawing Sheets

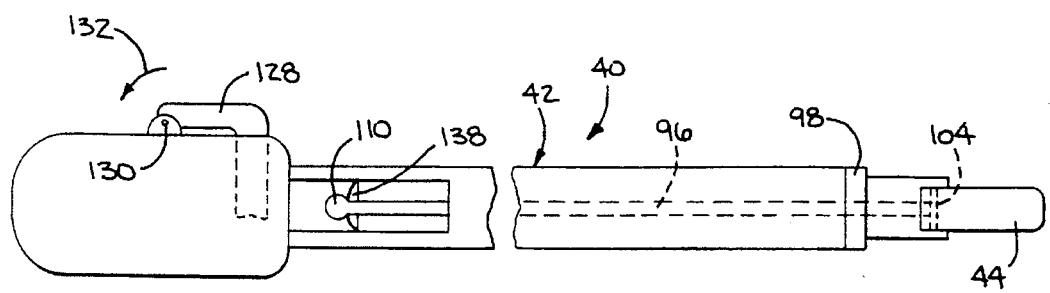
FIG. 4
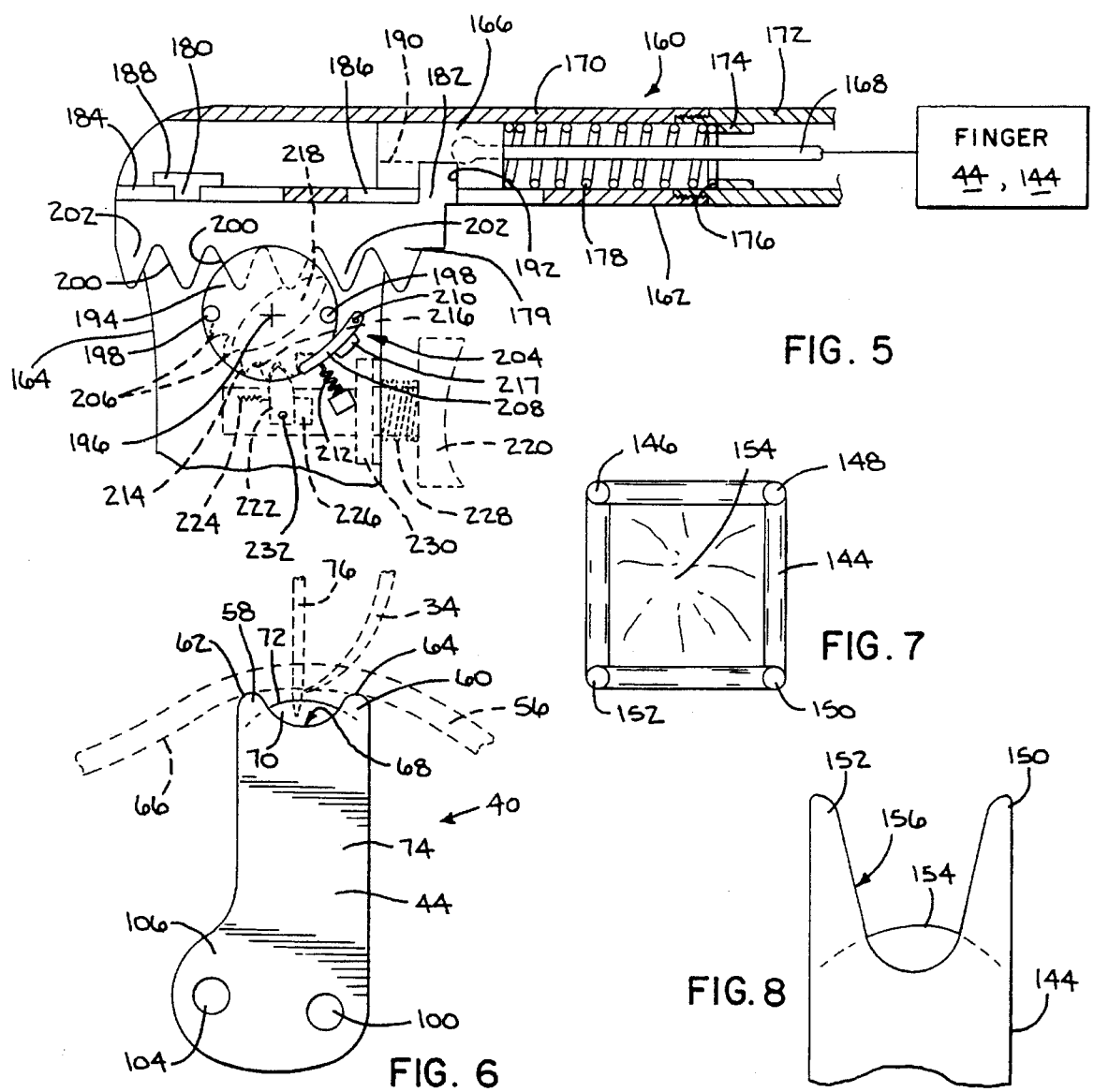
FIG. 5
FIG. 7
FIG. 6
FIG. 8

METHOD OF SUSPENDING A PELVIC ORGAN AND INSTRUMENT FOR PERFORMING THE METHOD

BACKGROUND OF THE INVENTION

1. Field of the Invention

This invention relates to surgical instruments and, more particularly, to an instrument that can be used to facilitate suturing and repositioning of a tissue that is accessed through a cavity bounded by the tissue. The invention is also directed to a method of using the instrument, as to assist suturing of vaginal tissue to stable pelvic structure.

2. Background Art

Structural defects of the female pelvis cause a variety of clinical problems including stress urinary incontinence, bladder prolapse or cystocele, rectal prolapse or rectocele, intestinal herniation or enterocele and prolapse of the vaginal vault after hysterectomy. Treatment of these problems has included a myriad of surgical procedures reflecting the inadequacy of any single procedure to effect a highly reliable cure. For instance, there are over 100 different operations for stress incontinence alone.

Vaginal procedures are often unsuccessful. They tend to imbricate attenuated fascia covering the organ but usually do not attach the organ to a stable structure found at a higher level, such as bone or strong fibrous ligament. A transvaginal repair by attaching the vagina to the higher (superior) sacrospinous ligament is effective. However, it is technically difficult and it is prone to serious vascular and nerve injury as it is carried out by feeling rather than visualization.

Abdominal procedures that attach the prolapsed tissue to stable bony or ligamentous areas found at a higher level as the pubic symphysis, Cooper's ligament or the sacrum are more effective. However, they are associated with the morbidity, disability and long hospital stay of a large abdominal incision.

Laparoscopic procedures have been recently described for treating a variety of these conditions. Laparoscopy provides excellent visualization of the target areas through a minimally invasive technique that can be performed on an outpatient basis with short recovery time, small cosmetic scars and potentially low morbidity. However, the development of laparoscopic techniques has been hampered by the lack of specialized instruments for the newly evolving procedures.

Reconstructive suspension procedures require elevation of the vagina to a higher level, closer to or adjacent to a fixed pelvic structure and subsequent attachment of the vagina to the fixed structure either directly with sutures or indirectly through the interposition of a biomembrane mesh. The biologically compatible mesh is attached to the fixed stable structure and to the prolapsed unstable vagina to create a membranous bridge that permits ingrowth of fibrous tissue and the creation of a strong permanent connection between the two sides.

Traditionally, vaginal elevation is accomplished with the human finger. Instruments such as a sponge stick or obturator cannot provide the appropriate position of vaginal elevation because they lack a knuckle or joint to change the direction of the tip from cephalad to anterior, or from cephalad to sideways, which is what is required.

Using the finger of an assistant to provide appropriate vaginal elevation and counter-traction for suturing has several disadvantages:

1. The finger may be punctured inadvertently by the suturing needle. This possibility causes the assistant and surgeon to be apprehensive during the suturing process. The surgeon may take less than optimum full thickness bites into the vaginal wall for fear of puncturing the assistant's finger.
2. The assistant may be fired or distracted and move the position of the finger to an inappropriate location inviting improper placement of sutures and related complications.
3. The assistant's finger may be too short to effect the necessary repositioning of the vagina.

SUMMARY OF THE INVENTION

One objective of the present invention is to provide a mechanical device that is useable in place of a human finger to optimally manipulate internal tissues, such as a vaginal wall during a suspension procedure. At the same time, it is desirable to provide an instrument that provides counter-traction to facilitate needle passage into tissue, such as vaginal and paravaginal tissue to obtain desired penetration thereof to allow for secure connection of the tissue to stable pelvic structure during a vaginal suspension procedure.

In one form, a surgical instrument is provided having a body, a tissue engaging and manipulating finger, and first structure for mounting the finger to the body. The finger has second structure thereon at first and second spaced locations to allow tissue engaged thereby to bridge the first and second spaced locations to allow a needle to be conveniently directed into a tissue engaged by the finger.

In one form, the first structure mounts the finger to the body for movement relative thereto between first and second positions, with the finger being movable from a location remote from the finger.

In one form, the finger pivots about an axis between its first and second positions.

In one form, the first structure includes an elongate rod, an actuator mounted to the body for movement between actuated and released positions, structure cooperating between the elongate rod and actuator for moving the elongate rod between first and second positions as the actuator moves between the actuated and released positions, and structure cooperating between the elongate rod and finger for moving the finger between its first and second positions as an incident of the elongate rod moving between its first and second positions.

Structure can be provided on the body for releasably maintaining the finger in each of the first and second positions and, in another form, a third position between the first and second positions.

In one form, the body includes a gripping portion that can be grasped by the hand of a user in such a manner that the actuator is accessible to and operable by a finger on the hand of a user grasping the surgical instrument.

In one form, the body has a pistol-type shape with an elongate body portion and a gripping portion extending transversely to the length of the elongate body portion.

To facilitate cleaning/sterilization of the finger, the finger can be removably connected to at least a portion of the body.

In one form, the finger has a body made from a first material and there is a needle backing material made from a second material that is different than the first material between the first and second locations.

A resilient or hard material may be disposed on the finger between the first and second locations. A resilient material, such as rubber, is penetrable by a needle so that the finger can be used to draw the needle through a tissue.

Alternatively, the needle backing material can be hard so as to stabilize the tissue and/or deflect the needle during a suturing operation. A convex surface can be provided on the finger for this purpose.

Further according to the invention, a surgical instrument is provided having an elongate body, an elongate tissue engaging and manipulating finger, and first structure for mounting the finger to the body so that the finger length extends transversely to the length of the body. The finger has an exposed surface thereon to engage a tissue and facilitate movement into engaged tissue by a suturing needle.

The finger can have two spaced projections to engage and support a tissue during a suturing operation.

The invention further contemplates a method of manipulating body tissue through a cavity bounded by the tissue. The method includes the steps of providing a surgical instrument having an elongate body with a finger at an end thereof. The finger has a length projecting transversely to the length of the body and a tissue engaging surface including structure thereon at first and second spaced locations to allow tissue engaged thereby to bridge between the first and second locations. The finger is directed into the tissue cavity against the tissue to stabilize the tissue. A needle is directed into tissue stabilized by the finger.

In one form, the tissue is a vaginal wall.

Further according to the invention, the needle is directed through the vaginal wall and into a fixed pelvic structure to effect attachment thereto.

During the procedure, the orientation of the finger relative to the body can be changed to facilitate the various steps.

The finger can be used during this procedure to elevate the vaginal wall.

BRIEF DESCRIPTION OF THE DRAWINGS

FIG. 4 is a plan view of the surgical instrument in FIG. 3;

FIG. 5 is a partial cross-sectional view of a modified form of surgical instrument, according to the present invention;

FIG. 6 is an enlarged, side elevation view of the finger on the inventive instrument shown engaged with tissue during a repositioning and/or suturing procedure;

FIG. 7 is an end view of a modified form of finger, according to the present invention; and FIG. 8 is a fragmentary, side elevation view of the finger in FIG. 7.

DETAILED DESCRIPTION OF THE DRAWINGS

Figure 1:
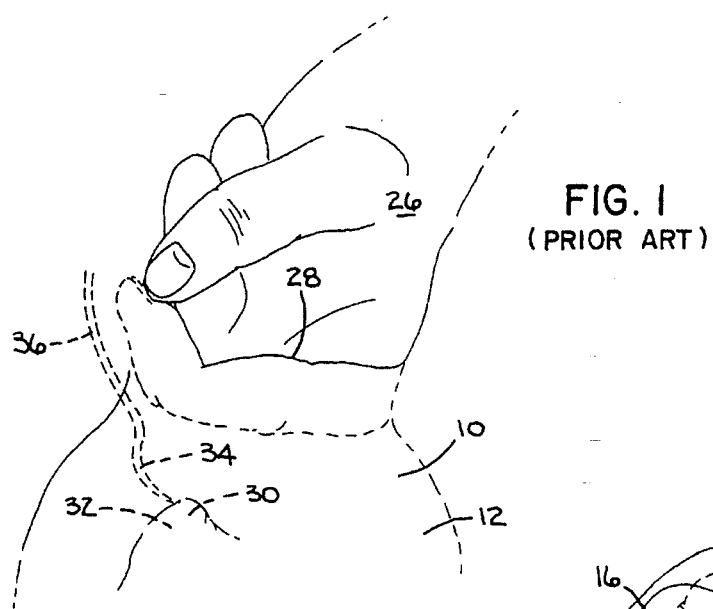
FIG. 1 is a side elevation view of a hand extending into the vaginal opening and with a finger thereon repositioning the vaginal wall and pressing a portion of the vaginal wall out to allow suturing thereof in conventional fashion.
Figure 2:
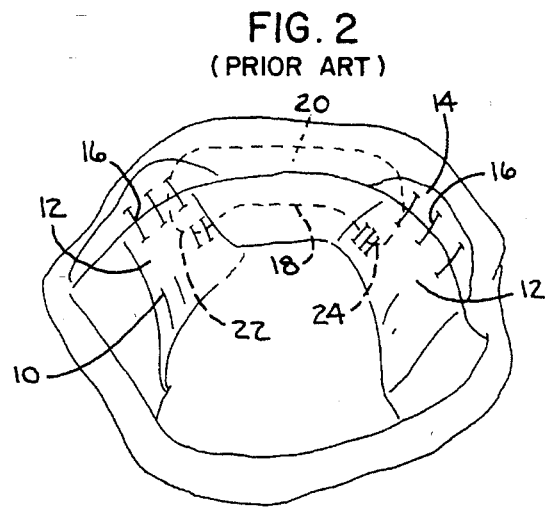
FIG. 2 is a front elevation view through an abdominal incision showing part of a vaginal wall attached to stable pelvic structure using conventional techniques.

In FIGS. 1 and 2, a known method of elevating a prolapsed vagina 10 is shown. The prolapsed vaginal wall 12 is elevated to be attached to stable pelvic structure, such as bony or ligamentous areas. As shown in FIG. 2, the vaginal wall 12 is attached to the Cooper's ligament 14 through a plurality of sutures 16.

Alternatively, a biomembrane mesh 18 is used to suspend the prolapsed vaginal wall 12 as from the pubic symphysis 20. The membrane 18 can be attached through the sutures 16 or other means such as staples to the stable pelvic structure. Spaced portions 22, 24 of the vaginal wall 12 are joined to the membrane 18 and optionally also to the Cooper's ligament 16. The vaginal wall 12 over time fuses with the membrane 18, which in turn unites with the stable pelvic structure to which it is attached to positively maintain the vaginal wall 12 in its desired elevated state.

Regardless of whether the vaginal wall 12 is sutured directly to the stable pelvic structure or indirectly supported thereon tit rough the membrane 18, elevation of the vagina 10 and suturing through the vaginal wall 12 are required. Typically, elevation and suturing assistance is afforded by an assistant. The hand 26 of the assistant is directed through the vaginal opening 28 to allow a finger 30 to engage that portion of the vaginal wall 12 that is to be sutured either directly to the stable pelvic structure or connected thereto through the membrane 18. The finger 30, after penetration of the vagina 10, is curled upwardly to press a portion 32 of the vaginal wall 12 outwardly to facilitate entry thereinto by a conventional suturing needle 34. Once the needle 34 penetrates the vaginal wall 12, the hand 26 of the user elevates the vagina 10 to place the vaginal wall portion 32 in close proximity to the pelvic structure to which it is to be attached.

As noted previously, the surgeon runs the risk of inadvertently puncturing the assistant's finger 30 with the needle 34 m attempting to get a full bite of the tissue. To prevent this situation, the surgeon may take a more shallow bite with the needle 34. As a result, the thread 36 of the suture may ultimately tear through the vaginal tissue.

The overall inconvenience and awkwardness associated with this conventional procedure can be readily seen.

According to the invention, an instrument is provided to perform the functions of the human assistant during the elevation of internal tissue, such as the vaginal wall 12.

Figure 3:
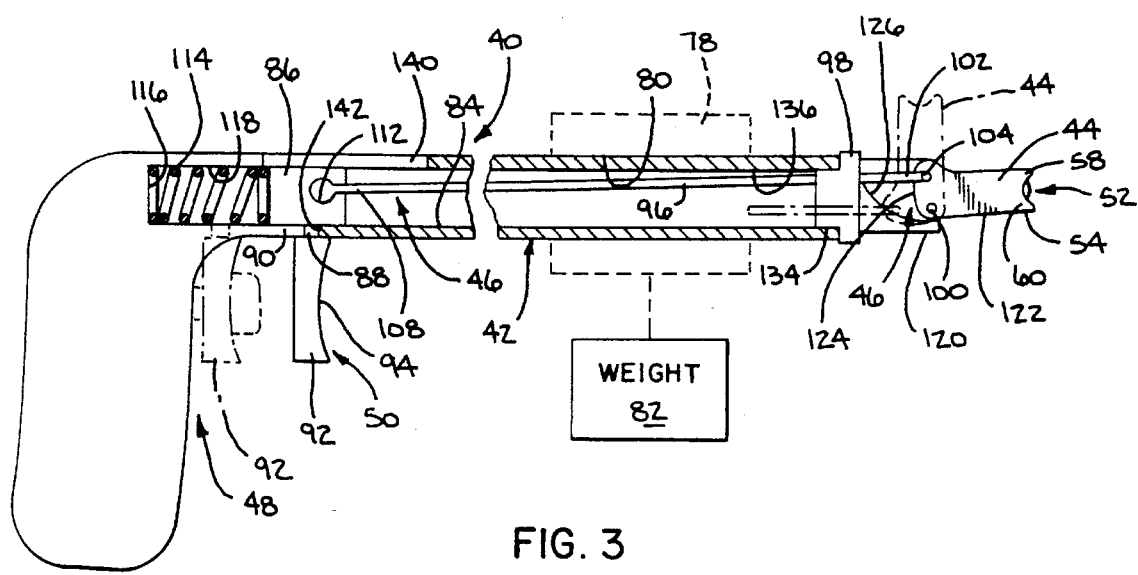
FIG. 3 is a cross-sectional view of a surgical instrument, according to the present invention, with a tissue engaging and manipulating finger thereon in two different positions.

One form of the inventive instrument is shown at 40 in FIGS. 3,4 and 6 The instrument 40 has an elongate body 42 to which a tissue engaging and manipulating finger 44 is mounted. A means at 46, for mounting the finger 44 to the body 42, mounts the finger 44 for movement between a first position, shown in solid lines in FIG. 3, and a second position, shown in phantom lines in FIG. 3.

The body 42 has a gripping portion 48 which can be grasped by the hand of a user operating the instrument 40. In this case, the gripping portion 48 extends transversely to the length of the body 42 to define a pistol-type arrangement. The user's hands grasping the gripping portion 48 is conveniently positioned to control the orientation of the instrument 40 as well as to operate an actuator 50, which is movable by a finger on the hand grasping the snipping portion 48, to thereby selectively move the finger 44 from its first position into its second position.

The finger 44 has means 52 at its distal end 54 for both a) positively engaging a tissue wall 56 to facilitate repositioning thereof and b) defining a stable support and backing structure to facilitate suturing of a tissue wall 56 engaged by a finger 44.

More particularly, the means 52 has at least two projections 58, 60 extending lengthwise with respect to the finger 44 and spaced at first and second locations. The projections 58, 60 have free ends 62, 64 which dig into the inside surface 66 of the tissue wall 56 to hold the finger 44 positively at a desired location on the tissue wall 56. The projections 58, 60 also define a space 68 therebetween to accommodate the needle 34 which is allowed to pass fully through the tissue 56 and into the space 68.

The invention contemplates variations of this basic structure. In FIG. 6, a needle backing element 70 is shown between the projections 58, 60. The needle backing element 70 can be defined in two different ways to perform two different functions. In one form, the needle backing element 70 is made from a hard material that is impenetrable by the needle 34. The element 70 has a convex surface 72 which, upon encountering the needle 34, deflects the needle 34, as between the projections 58, 60. This facilitates passage of the needle 34 fully through the tissue wall 56. This convex surface 72 also reinforces the tissue wall 56 between the projections 58, 60 to allow the needle 44 to penetrate a substantial distance into of the tissue wall 56 without extending fully therethrough.

The needle backing element 70 can also be made from a material that is different than that making up the body 74 of the finger. For example, the element 70 can be made from a resilient material that is penetrable by the curved needle 34 or a straight needle 76. With this arrangement, the surgeon can direct the needle 76 into the element 70 and then move the finger 44 downwardly in FIG. 6 to draw the needle 76 fully through the tissue wall 56.

In operation, the surgeon grasps the gripping portion 48 on the instrument 40 and directs the finger 44 in the solid line position of FIG. 3 into the vagina or in any cavity bounded by a tissue which is to be repositioned and/or sutured. The surgeon can then, by operating the actuator 50, move the finger 44 to the phantom line position in FIG. 3 and can then press the distal end 54 of the finger 44 against a tissue 56 to be repositioned and/or sutured. The suturing process can be performed on the engaged tissue wall 56.

The surgeon can conveniently use the instrument 40 to reposition the tissue wall 56. Since the finger 44 presses into the tissue wall 56, the tissue wall 56 is held relatively positively thereby so that the portion of the tissue wall 56 engaged by the finger 44 will follow movement of the finger 44 as it is repositioned by the surgeon. In the case of a vaginal elevation, the finger 44 can be used to conveniently situate the vaginal wall 12 in close proximity to stable pelvic structure to allow connection thereto.

As can be seen, the instrument 40 can be used to provide all the advantages of manual human manipulation without the inherent inconvenience and dangers associated therewith.

To add further versatility to the instrument 40, a support sleeve 78 can be directed into a cavity, such as the vagina. The sleeve 78 has a through opening 80 to accept the instrument 40. The sleeve 78 is borne downwardly by a weight 82 so as to situate the sleeve 78 in a consistent desired orientation relative to the cavity which it penetrates. A preferred structure for accomplishing this is shown in my co-pending application Ser. No. 08/062,923, entitled "Support For Surgical Instrument". With this arrangement, the instrument 40 can be consistently maintained in a desired orientation without user intervention, as to facilitate a suturing process.

Various details of the instrument 40 will now be described. The body 42 has a generally cylindrical configuration and an internal bore 84, of substantially uniform cross section, for guidingly receiving a block 86. The block 86 is movable in a fore and aft direction within the bore 84. The block has a leg 88 that extends through a slot 90 in the body 42 and terminates in a trigger 92 with a curved forward wall 94 that is conveniently pressed in a rearward direction by a finger on the hand grasping the gripping portion 48 of the body 42.

The block 86 transmits a repositioning force on the finger 44 through an elongate rod 96. The rod 96 extends through an end fitting 98 to which the finger 44 is connected through a pin 100 for pivoting movement about an axis defined by the pin 100 between the solid and phantom line positions in FIG. 3. The distal end 102 of the rod 96 is connected by a pin 104 to a wall 106 on the finger body 74 at a location offset from the pivot pin 100.

The proximal end 108 of the rod 96 has an end fitting 110, in the shape of a ball, which is guided in universal movement relative to the block 86 within a socket 112 defined in the block 86. With this arrangement, the rod 96 follows fore and aft movement of the block 86.

The block 86 is normally biased in a forward direction by a coil spring 114 acting between the block 86 and a forwardly facing shoulder 116 defined by a blind bore 118 in the body 42. Forward movement of the block 86 drives the rod 96 forwardly to pivot the finger 44 in a clockwise direction in FIGS. 3 and 6 so that the finger 44 assumes the solid line position in FIG. 3. The fitting 98 has a stop 120 which abuts a surface 122 of the finger 44 to arrest clockwise movement of the finger 44 so that the finger 44 consistently assumes the solid line position in FIG. 3 in its normal state.

By drawing the trigger 92 rearwardly, the block 86 and rod 96 are advanced rearwardly, which causes the finger 44 to pivot in a counterclockwise direction about the pin 100 until a stop surface 124 on the finger 44 abuts the surface 126 on the fitting 98, at which point the length of the finger 44 is substantially at right angles to its normal position.

An L-shaped latch 128 is pivotably connected to the body 42 by a pin 130 and is movable selectively into and out of the position shown in FIGS. 3 and 4, wherein it maintains the trigger 92 in its rearwardmost position and the finger 44 in the phantom line position of FIG. 3. By pivoting the latch element 128 in the direction of arrow 132 in FIG. 4, the trigger 92 can be released to allow the block 86 and rod 96 to move forwardly under the force of the compression spring 114.

To facilitate cleaning/sterilization of the finger 44, the fitting 98, with the finger 44 thereon, is made to be removable from the body 42. In this case, the fitting 98 has a reduced diameter portion 134 which is fictionally engaged with the inside body surface 136 bounding the bore 84. The ball 110 on the rod 96 is removable from the socket 112 by upward movement thereof through a top entryway 138 in the block 86. A slot 140 at the upper portion of the body 42 permits access to the ball 110 to facilitate insertion and removal thereof.

Once the user removes the ball 110 from the socket 112, the fitting 98 can be separated from the body 42 to allow the rod 96 to be pulled forwardly through and out of the bore 84. Reassembly involves a simple reversal of these steps. With the rod 96 and fitting 98 disconnected, the block 86 is limited in forward movement by a shoulder 142 bounding the slot 90 within which the leg 88 projects. The leg 88 abuts to the shoulder 142 to confine forward movement of the block 86.

With the above arrangement, the pivot axis for the finger 44 can be varied as desired. This can be accomplished by simply rotating the fitting 98 relative to the body 42 in which it is received.

One variation of the inventive structure is shown in FIGS. 7 and 8. In this case, a modified form of finger 144 is shown. The finger 144 has four projections 146, 148, 150, 152 which define a tissue support. A semi-spherical surface 154 resides between the projections 146, 148, 150, 152 and defines either a backing/deflecting surface or a penetrable element to accept a needle. The finger 144 functions in essentially the same manner as the finger 44 but has additional support by reason of the additional projections 146, 148, 150, 152 and a deeper space 156, as shown between the exemplary projections, 150, 152.

A further modified form of instrument, according to the present invention, is shown at 160 in FIG. 5. The instrument 160 has a body 162 with a gripping portion 164 as in the previously described embodiment. A translatable block 166 is used to advance and retract a rod 168, which operates a finger 44, 144.

The instrument body 162 is defined by threadably joined parts 170, 172. The forward body part 172 has a reduced diameter section 174 defining an internal annular shoulder 176 to abut to a coil spring 178 which abuts to the block 166 to thereby normally urges the block 166 on the rod 168 carried thereby in a rearward direction. The connection of the rod 168 to the block 166 and the rod 168 to the finger 44, 144 can be the same as that described for the instrument 40, previously described.

A toothed rack 179 is guided by spaced legs 180, 182 in fore and aft movement relative to the body 162. The legs 180, 182 are guided in slots 184, 186 extending through the body 162. An enlargement 188 on the leg 180 prevents separation of the rack 179 from the body 162. The leg 182 is received in a rearwardly opening slot 190 in the block 166. The leg 182 abuts a rearwardly facing surface 192 bounding the slot 190 to drive the block 166 forwardly.

Forward movement of the rack 179 and block 166 and rod 168 is accomplished through a wheel 194 which is rotatable about an axis 196. The wheel 194 has diametrically opposite pins 198 which alternately engage drive surfaces 200 on the rack teeth 202 as the drive wheel 194 is rotated about its axis 196.

The drive wheel 194 has an associated ratchet mechanism 204. The ratchet mechanism 204 includes teeth 206 on the wheel 194 spaced equidistantly about the circumference thereof. The teeth 206 are engaged by a ratchet arm 208 that is pivotable about a pin 210 and biased normally by a spring 212 into engagement with the teeth 206.

As the wheel 194 is rotated in a clockwise direction in FIG. 5, the arm 208 rides over the leading tooth surfaces 214 and is repetitively driven by the spring 212 between adjacent teeth 206 to engage the trailing tooth surfaces 216. The cooperating teeth 206 and arm 208 thus maintain the position of the finger 44, 144 in a plurality of different positions between and including the solid and phantom line positions shown in FIG. 3.

A tab 217 is provided on the arm 208 and allows the arm 208 to be manually pivoted against the force of the spring 212 out of engagement with the teeth 206 to allow the wheel 194 to be rotated in a counterclockwise direction i.e. to advance the rack 179 in a rearward direction.

An optional graspable tab 218 is provided on the wheel 194 to facilitate rotation thereof. Alternatively, a trigger 220 can be incorporated to rotate the wheel 194. The trigger 220 carries a ratchet arm 222 that is normally biased by a spring 224 against a stop 226 to an engaged position. Right to left movement of the trigger 220 in FIG. 5 causes the arm 222 to engage one of the teeth 206 mid chive the wheel 194 in a clockwise direction about the axis 196.

A spring 228 acts between the gripping portion 164 and the trigger 220 to normally urge the trigger 220 from left to fight in FIG. 5. Forward movement is limited by an internal, enlarged bead 230 on the trigger 220. As the trigger 220 advances from left to right in FIG. 5, the arm 222 is allowed to pivot in a counterclockwise direction about the pin 232 to thereby bring it out of blocking engagement with the teeth 206.

With the instrument 160, the body parts 170, 172 can be separated to allow the block 166, rod 168 and finger 144 to be advanced forwardly through and separated from the body part 170, as to facilitate cleaning/sterilization of the instrument 160. Re-assembly of the instrument 160 can be readily accomplished by reversing the above steps.

The foregoing disclosure of specific embodiments is intended to be illustrative of the broad concepts comprehended by the invention.

I claim:

1. A surgical instrument comprising:

a body;

a tissue engaging and manipulating finger; and first means for mounting the finger to the body, said finger having second means thereon including first, second and third projections having unjoined free ends which are in fixed, spaced relationship to allow tissue engaged thereby to bridge the first, second and third projections to allow a needle to be directed into a tissue engaged by the finger, wherein the finger has a body made from a first material and there is a second material that is different than the first material on the finger between at least two of the projections to allow a needle directed through tissue engaged by the finger to be directed against the second material.

2. The surgical instrument according to claim 1 wherein the second material is a resilient material that is penetrable by a suturing needle.

3. The surgical instrument according to claim 2 wherein the resilient material is rubber.

4. A surgical instrument comprising:

a body;

a tissue engaging manipulating finger; and first means for mounting the finger to the body, said finger having second means thereon including first, second and third projections having unjoined free ends which are in fixed, spaced relationship to allow tissue engaged thereby to bridge the first, second and third projections to allow a needle to be directed into tissue engaged by the finger, wherein there is a convex surface on the finger to deflect a needle passed through tissue engaged by the finger away from the finger.

5. A surgical instrument comprising:

a body;

a tissue engaging and manipulating finger; and first means for mounting the finger to the body, said finger having second means thereon including first, second and third projections having unjoined free ends which are in fixed, spaced relationship to allow tissue engaged thereby to bridge the first, second and third projections to allow a needle to be directed into a tissue engaged by the finger, wherein the first means comprises means for mounting the finger to the body for movement relative thereto between first and second positions.

wherein the first means comprises means for mounting the finger to the body for pivoting movement about a first axis between the first and second positions.

6. The surgical instrument according to claim 5 including means on the body for repositioning the finger selectively between said first and second positions from a location remote from said finger.

7. The surgical instrument according to claim 5 wherein the first means includes means for removably connecting the finger to at least a portion of the body.

8. The surgical instrument according to claim 5 including means on the body for biasing the finger towards one of the first and second positions.

9. The surgical instrument according to claim 5 including means on the body for releasably maintaining the finger in each of the first and second positions.

10. The surgical instrument according to claim 5 including means on the body for releasably maintaining the finger in a third position between the first and second positions.

11. A surgical instrument comprising:

a body:

a tissue engaging and manipulating finger; and first means for mounting the finger to the body, said finger having second means thereon including first, second and third projections having unjoined free ends which are in fixed, spaced relationship to allow tissue engaged thereby to bridge the first, second and third projections to allow a needle to be directed into a tissue engaged by the finger, wherein the first means comprises means for mounting the finger to the body for movement relative thereto between first and second positions, wherein the first means includes an elongate rod, an actuator, means for mounting the actuator to the body for movement between actuated and released positions, means cooperating between the elongate rod and actuator for moving the elongate rod between first and second positions as the actuator moves between the actuated and released positions, and means cooperating between the elongate rod and finger for moving the finger between the first and second positions as an incident of the elongate rod moving between its first and second positions.

12. The surgical instrument according to claim 11 wherein the body includes a gripping portion that can be grasped by the hand of a user in such a manner that the actuator is accessible to and operable by a finger on the hand of a user grasping the surgical instrument.

13. The surgical instrument according to claim 12 wherein the body has a pistol-type shape with an elongate body portion and a gripping portion extending transversely to the length of the elongate body portion.

14. A method of manipulating body tissue through a cavity bounded by the tissue, said method comprising the steps of:

providing a surgical instrument having an elongate body with a finger at an end thereof, said finger having a length extending transversely to the length of the body and first, second, and third projections having unjoined free ends which are in fixed, spaced relationship to allow tissue engaged thereby to bridge and be supported by the first, second and third projections;

directing the finger into the tissue cavity and bearing the first, second and third projections on the finger against the tissue to stabilize the tissue; and directing a needle into the tissue stabilized by the finger between at least two of the projections.

15. The method of manipulating body tissue according to claim 14 wherein the step of directing a needle into the tissue comprises the step of directing a needle through a vaginal wall.

16. The method of manipulating body tissue according to claim 15 including the step of attaching the vaginal wall to a fixed pelvic structure by directing the needle into a fixed pelvic structure after the needle is directed into tissue engaged by the finger.

17. The method of manipulating body tissue according to claim 16 including the step of lifting the vaginal wall with the finger to facilitate connection of the vagina to a fixed pelvic structure.

18. The method of manipulating body tissue according to claim 16 wherein the step of providing a surgical instrument includes the step of providing a resilient material on the finger and including the step of directing the needle into the resilient material after it is directed into the tissue stabilized by the finger.

19. The method of manipulating body tissue according to claim 16 wherein the step of providing a surgical instrument comprises the step of providing a surgical instrument wherein the step of providing a surgical instrument comprises the step of providing a surgical instrument wherein the free ends on the first, second and third projections are spaced relative to each other so that they do not reside in a single line.

20. The method of manipulating body tissue according to claim 14 including the step of varying the orientation of the finger relative to the body from a first orientation, wherein the length of the finger is substantially aligned with the length of the body, to a second orientation, wherein the length of the finger extends transversely to the length of the body, after the finger is directed into the cavity.

* * * * *